United States Patent
Hamada et al.

(10) Patent No.: US 9,150,502 B2
(45) Date of Patent: Oct. 6, 2015

(54) URETHANE COMPOUND AND METHOD FOR PRODUCING THE SAME, AND ISOCYANATE AND METHOD FOR PRODUCING THE SAME

(75) Inventors: Tetsuya Hamada, Ichihara (JP); Mitsuaki Chida, Mobara (JP); Souta Itou, Mobara (JP); Yoshiki Shimokawatoko, Chiba (JP); Koichi Murayama, Chiba (JP); Hiroshi Takeuchi, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 208 days.

(21) Appl. No.: 13/258,453

(22) PCT Filed: Mar. 17, 2010

(86) PCT No.: PCT/JP2010/054531
§ 371 (c)(1),
(2), (4) Date: Sep. 21, 2011

(87) PCT Pub. No.: WO2010/110142
PCT Pub. Date: Sep. 30, 2010

(65) Prior Publication Data
US 2012/0010427 A1    Jan. 12, 2012

(30) Foreign Application Priority Data

Mar. 26, 2009 (JP) .................. 2009 077456
Jan. 25, 2010 (JP) .................. 2010 013059

(51) Int. Cl.
*C07C 263/04* (2006.01)
*C07C 269/04* (2006.01)

(52) U.S. Cl.
CPC ............. *C07C 263/04* (2013.01); *C07C 269/04* (2013.01)

(58) Field of Classification Search
CPC .......................... C07C 263/04; C07C 269/04
USPC .......................................... 560/158, 345, 360
See application file for complete search history.

(56) References Cited

U.S. PATENT DOCUMENTS

| 4,081,472 | A |   | 3/1978 | Tsumura et al. |
| 4,278,805 | A | * | 7/1981 | Merger et al. ............... 560/25 |
| 4,286,073 | A |   | 8/1981 | Coe |
| 4,375,000 | A |   | 2/1983 | Merger et al. |
| 4,611,079 | A |   | 9/1986 | Merger et al. |
| 2001/0005761 | A1 |   | 6/2001 | Laqua et al. |

FOREIGN PATENT DOCUMENTS

| CA | 1144-562 | * | 4/1983 | ............. C07C 125/06 |
| CA | 1144562 |  | 4/1983 | |
| EP | 0 279 40 A1 |  | 5/1981 | |
| EP | 0 437 258 A1 |  | 7/1991 | |
| JP | 55-149241 |  | 11/1980 | |
| JP | 57-114561 |  | 7/1982 | |
| JP | 57-158751 |  | 9/1982 | |
| JP | 04-018064 |  | 1/1992 | |
| JP | 08-217744 |  | 8/1996 | |
| JP | 11-514659 |  | 12/1999 | |

OTHER PUBLICATIONS

Firouzabadi et al. Solid trichlorotitanium (IV) trifluoromethanesulfonate TiCl3(OTf) catalyzed efficient acylation of -OH and -SH: Direct esterification of alcohols with carboxylic acids and transesterification of alcohols with esters under neat conditions, Journal of Molecular Catalysis A: Chemical, 289, 61-68 (2008).*
Oohashi et al., Efficient Method for the Esterification of Carboxylic Acids with Alcohols Using Di-thienyl Carbonate Promoted by Catalytic Amounts of DMAP and Hf(OTf)4, Chemistry Letters, 34(2), 190-191, 2005.*
Shekarriz et al., "Esterification of carboxylic acids with alcohols under microwave irradiation in the presence of zinc triflate," J. Chem. Research (S), 172-173, 2003.*
Ma et al., "Study on catalytic properites of zinc sulfonates in synthesizing chloroacetates," Huagong Keji (2005), 13(1), 49-52.*
Translation of Ma et al., "Study on catalytic properites of zinc sulfonates in synthesizing chloroacetates," Huagong Keji (2005), 13(1), 49-52.*
International Search Report in PCT/JP2010/054531 dated Apr. 27, 2010.
Supplementary European Search Report EP 10 75 5940.3 dated Oct. 2, 2012.
Ingo Krossing et al., "Noncoordinating Anions—Fact or Fiction? A Survey of Likely Candidates", Angew. Chem. Int. Ed., 2004, 43, pp. 2066-2090.
Taiwanese Office Action dated Apr. 7, 2014 issued in Taiwanese Application No. 099109056.

* cited by examiner

*Primary Examiner* — Paul A Zucker
*Assistant Examiner* — Mark Luderer
(74) *Attorney, Agent, or Firm* — Foley & Lardner LLP

(57) ABSTRACT

A method for producing urethane compounds includes allowing a primary amine, a urea and/or an N-unsubstituted carbamate, and an alcohol to react in the presence of a compound containing a noncoordinating anion and a metal atom as a catalyst.

6 Claims, No Drawings

URETHANE COMPOUND AND METHOD FOR PRODUCING THE SAME, AND ISOCYANATE AND METHOD FOR PRODUCING THE SAME

TECHNICAL FIELD

The present invention relates to a method for producing urethane compounds, urethane compounds obtained by the urethane compound producing method, a method for producing isocyanates using the urethane compound, and isocyanates obtained by the isocyanate producing method.

BACKGROUND ART

Conventionally, urethane compounds such as alkyl carbamates are useful organic compounds as industrial raw materials having a wide variety of applications such as a raw material for medicine and agricultural chemicals, a raw material for various fine chemicals, and a reagent for analysis of alcohols.

In recent years, various studies have been made to use such alkyl carbamate as a raw material for phosgene-free production of isocyanates.

Specifically, isocyanates are organic compounds containing isocyanate groups, widely used as raw materials of polyurethane, and industrially produced by a reaction between amine and phosgene (phosgene method).

The phosgene is, however, highly toxic and corrosive, resulting in inconvenient handling. Therefore, as an alternative to the phosgene method, an economical method for producing isocyanates has been recently proposed that produces an isocyanate by allowing amine, urea or carbamate, and alcohol to react to produce urethane compounds, and thereafter thermally decomposing the urethane compounds thus produced.

As the method for producing urethane compounds, it has been proposed, for example, a method for producing 2,4-di-(ethoxycarbonylamino)-toluol by allowing 2,4-diaminotoluol, carbamic acid ethyl ester, and ethanol to react in the presence of iron(II) acetate which is a Lewis acid catalyst made of a metal atom cation and a coordinating anion (see, for example, the following Patent Document 1, Examples 36).

Further, it has been proposed, for example, a method for producing 2,4-bis-(n-hexoxycarbonyl-amino)-toluene by allowing diaminotoluene, urea, and n-hexanol to react in the presence of zinc octoate which is a Lewis acid catalyst made of a metal atom cation and a coordinating anion (see, for example, the following Patent Document 2, Example 11).

Patent Document 1: Japanese Unexamined Patent Publication No. 55-149241
Patent Document 2: Japanese Unexamined Patent Publication No. 57-114561

DISCLOSURE OF THE INVENTION

Problems to be Solved

In the method described in the above-mentioned Patent Document 1, however, in order to produce 2,4-di-(ethoxycarbonylamino)-toluol in high yield, each of the above-mentioned components needs to react under high-temperature and high-pressure conditions for a long period of time. Therefore, the cost inevitably increases and the method described in the above-mentioned Patent Document 1 is unsuitable for industrial production of urethane compounds.

In the method described in the above-mentioned Patent Document 2, in order to obtain 2,4-bis-(n-hexoxycarbonyl-amino)-toluene in high yield, each of the above-mentioned components needs to react under high-temperature condition for a long period of time. Therefore, as with the method described in Patent Document 1, the cost inevitably increases and the method described in the above-mentioned Patent Document 2 is unsuitable for industrial production of urethane compounds.

The above-mentioned Patent Document 2 also proposes that 2,4-bis-(n-hexoxycarbonyl-amino)-toluene is produced for a relatively short period of time by allowing each of the above-mentioned components to react in a pressure apparatus (see, for example, the above-mentioned Patent Document 2, Example 7).

In the method described in the above-mentioned Patent Document 2, however, even if the pressure in the apparatus is increased to the required reaction pressure, 2,4-bis-(n-hexoxycarbonyl-amino)-toluene cannot be obtained in high yield. Therefore, again, the method described in Patent Document 2 is unsuitable for industrial production of urethane compounds.

In view of these disadvantages, it is, therefore, an object of the present invention to provide a method for producing urethane compounds that allows urethane compounds to be produced at low cost and high yield for a short period of time by a simple process, urethane compounds obtained by the urethane compound producing method, a method for producing isocyanates that allows isocyanates industrially used to be produced using the urethane compound, and isocyanates obtained by the isocyanate producing method.

Means for Solving the Problem

The method for producing urethane compounds of the present invention includes allowing a primary amine, a urea and/or an N-unsubstituted carbamate, and an alcohol to react in the presence of a compound containing a noncoordinating anion and a metal atom as a catalyst.

In the method for producing urethane compounds of the present invention, it is preferable that the primary amine is represented by the following general formula (1); the N-unsubstituted carbamate is represented by the following general formula (2); the alcohol is represented by the following general formula (3); and the compound is represented by the following general formula (4):

$$R^1\text{—}(NH_2)l \qquad (1)$$

(wherein $R^1$ represents an aliphatic hydrocarbon group having 1 to 15 total carbon atoms, an alicyclic-containing hydrocarbon group having 3 to 15 total carbon atoms, or an aromatic ring-containing hydrocarbon group having 6 to 15 total carbon atoms; and l represents an integer of 1 to 6.)

$$R^2O\text{—}CO\text{—}NH_2 \qquad (2)$$

(wherein $R^2$ represents an aliphatic hydrocarbon group having 1 to 16 total carbon atoms, or an aromatic hydrocarbon group having 6 to 16 total carbon atoms.)

$$R^3\text{—}OH \qquad (3)$$

(wherein $R^3$ represents an aliphatic hydrocarbon group having 1 to 16 total carbon atoms, or an aromatic hydrocarbon group having 6 to 16 total carbon atoms.) and

$$MX^1{}_mX^2{}_{n-m} \qquad (4)$$

(wherein M represents a metal atom belonging to Groups 1 to 16 of the Periodic Table; $X^1$ represents a noncoordinating anion; $X^2$ represents a ligand; m represents an integer of 1 to n; and n represents a valence of M.)

In the method for producing urethane compounds of the present invention, it is preferable that in the general formula (4), $X^1$ is a noncoordinating anion represented by the following general formula (5):

$$R^4SO_3^-  \quad (5)$$

(wherein $R^4$ represents a substituent having a substituent constant σ ranging from −0.1 to +0.7.)

In the method for producing urethane compounds of the present invention, it is preferable that in the general formula (5), $R^4$ is an aliphatic hydrocarbon group having 1 to 16 total carbon atoms or an aromatic hydrocarbon group having 6 to 16 total carbon atoms, which contain at least one fluorine atom.

In the method for producing urethane compounds of the present invention, it is preferable that in the general formula (4), M is a metal atom belonging to Group 4 or 12 of the Periodic Table.

In the method for producing urethane compounds of the present invention, it is preferable that in the general formula (1), l is 2.

In the method for producing urethane compounds of the present invention, it is preferable that in the general formula (1), $R^1$ is an aromatic ring-containing hydrocarbon group having 6 to 15 total carbon atoms.

In the method for producing urethane compounds of the present invention, it is preferable that an amount of the catalyst ranges from 0.000001 to 0.1 mol based on 1 mol of the primary amine.

The present invention also includes a method for producing isocyanates including the steps of producing urethane compounds by the method for producing urethane compounds described above; and thermally decomposing thus-produced urethane compounds to produce isocyanates.

The present invention also includes urethane compounds obtained by the method for producing urethane compounds described above.

The present invention also includes isocyanates obtained by the method for producing isocyanates described above.

Effect of the Invention

According to the method for producing urethane compounds of the present invention, urethane compounds can be produced at low cost and high yield for a short period of time by a simple process. Therefore, the present invention can be suitably used as an industrial method for producing urethane compounds.

Further, according to the method for producing isocyanates of the present invention, polyisocyanates industrially used as raw materials of polyurethane can be produced easily and efficiently.

EMBODIMENT OF THE INVENTION

The method for producing urethane compounds (also referred to as carbamates or carbamic acid esters) of the present invention will be first described in detail. According to the method for producing urethane compounds of the present invention, a primary amine, a urea and/or an N-unsubstituted carbamate, and an alcohol are allowed to react in the presence of a catalyst.

The primary amine used in the present invention is an amino group-containing organic compound which has at least one primary amino group, and is represented, for example, by the following general formula (1):

$$R^1—(NH_2)l \quad (1)$$

(wherein $R^1$ represents an aliphatic hydrocarbon group having 1 to 15 total carbon atoms, an alicyclic-containing hydrocarbon group having 3 to 15 total carbon atoms, or an aromatic ring-containing hydrocarbon group having 6 to 15 total carbon atoms; and l represents an integer of 1 to 6.)

In the above formula (1), $R^1$ is selected from the aliphatic hydrocarbon group having 1 to 15 total carbon atoms, the alicyclic-containing hydrocarbon group having 3 to 15 total carbon atoms, and the aromatic ring-containing hydrocarbon group having 6 to 15 total carbon atoms. $R^1$ may contain a stable linkage such as an ether linkage, a thioether linkage, or an ester linkage in the hydrocarbon group, and may be substituted with a stable functional group (described later).

In $R^1$, examples of the aliphatic hydrocarbon group having 1 to 15 total carbon atoms include linear or branched, monovalent to hexavalent aliphatic hydrocarbon groups having 1 to 15 total carbon atoms.

In the above formula (1), examples of the primary amine whose $R^1$ is an aliphatic hydrocarbon group having 1 to 15 total carbon atoms include aliphatic amines having 1 to 15 total carbon atoms.

Examples of the aliphatic amine include linear or branched aliphatic primary monoamines such as methylamine, ethylamine, n-propylamine, iso-propylamine, butylamine, pentylamine, hexylamine, n-octylamine, 2-ethylhexylamine, decylamine, dodecylamine, and tetradecylamine; aliphatic primary diamines such as 1,2-diaminoethane, 1,3-diaminopropane, 1,4-diaminobutane (1,4-tetramethylenediamine), 1,5-diaminopentane (1,5-pentamethylenediamine), 1,6-diaminohexane (1,6-hexamethylenediamine), 1,7-diaminoheptane, 1,8-diaminooctane, 1,9-diaminononane, 1,10-diaminodecane, 1,12-diaminododecane, 2,2,4-trimethyl hexamethylenediamine, 2,4,4-trimethyl hexamethylenediamine, and tetramethylenediamine; and aliphatic primary triamines such as 1,2,3-triaminopropane, triaminohexane, triaminononane, triaminododecane, 1,8-diamino-4-aminomethyloctane, 1,3,6-triaminohexane, 1,6,11-triaminoundecane, and 3-aminomethyl-1,6-diaminohexane.

In $R^1$, examples of the alicyclic-containing hydrocarbon group having 3 to 15 total carbon atoms include monovalent to hexavalent alicyclic-containing hydrocarbon groups having 3 to 15 total carbon atoms.

The alicyclic-containing hydrocarbon group contains at least one alicyclic hydrocarbon in the hydrocarbon group and, for example, an aliphatic hydrocarbon group or the like may be bonded to the alicyclic hydrocarbon. In such case, the amino group in the primary amine may be either directly bonded to the alicyclic hydrocarbon or bonded to an aliphatic hydrocarbon group which is bonded to the alicyclic hydrocarbon, or both.

In the above formula (1), examples of the primary amine in which $R^1$ is an alicyclic-containing hydrocarbon group having 3 to 15 total carbon atoms include alicyclic amines having 3 to 15 total carbon atoms.

Examples of the alicyclic amine include alicyclic primary monoamines such as cyclopropylamine, cyclobutylamine, cyclopentylamine, cyclohexylamine, and hydrogenated toluidine; alicyclic primary diamines such as diaminocyclobutane, isophoronediamine (3-aminomethyl-3,5,5-trimethylcyclohexylamine), 1,2-diaminocyclohexane, 1,3-diaminocyclohexane, 1,4-diaminocyclohexane, 1,3-bis(aminomethyl)cyclohexane, 1,4-bis(aminomethyl)cyclohexane, 4,4'-methylenebis(cyclohexylamine), 2,5-bis (aminomethyl)bicyclo[2,2,1]heptane, 2,6-bis(aminomethyl) bicyclo[2,2,1]heptane, hydrogenated 2,4-tolylenediamine, and hydrogenated 2,6-tolylenediamine; and alicyclic primary triamine such as triaminocyclohexane.

In $R^1$, examples of the aromatic ring-containing hydrocarbon group having 6 to 15 total carbon atoms include monovalent to hexavalent aromatic ring-containing hydrocarbon groups having 6 to 15 total carbon atoms.

The aromatic ring-containing hydrocarbon group contains at least one aromatic hydrocarbon in the hydrocarbon group and, for example, an aliphatic hydrocarbon group or the like may be bonded to the aromatic hydrocarbon. In such case, the amino group in the primary amine may be either directly bonded to the aromatic hydrocarbon or bonded to an aliphatic hydrocarbon group which is bonded to the aromatic hydrocarbon, or both.

In the above formula (1), examples of the primary amine in which $R^1$ is an aromatic ring-containing hydrocarbon group having 6 to 15 total carbon atoms include aromatic amines having 6 to 15 total carbon atoms and aralkyl amines having 6 to 15 total carbon atoms.

Examples of the aromatic amine include aromatic primary monoamines such as aniline, o-toluidine (2-methylaniline), m-toluidine (3-methylaniline), p-toluidine (4-methylaniline), 2,3-xylidine (2,3-dimethylaniline), 2,4-xylidine (2,4-dimethylaniline), 2,5-xylidine (2,5-dimethyl aniline), 2,6-xylidine (2,6-dimethylaniline), 3,4-xylidine (3,4-dimethylaniline), 3,5-xylidine (3,5-dimethylaniline), 1-naphthylamine, and 2-naphthylamine; and aromatic primary diamines such as 2,4-tolylenediamine, 2,6-tolylenediamine, 4,4'-diphenylmethanediamine, 2,4'-diphenylmethanediamine, 2,2'-diphenylmethanediamine, 4,4'-diphenyletherdiamine, 2-nitrodiphenyl-4,4'-diamine, 2,2'-diphenylpropane-4,4'-diamine, 3,3'-dimethyldiphenylmethane-4,4'-diamine, 4,4'-diphenylpropanediamine, m-phenylenediamine, p-phenylenediamine, naphthylene-1,4-diamine, naphthylene-1,5-diamine, and 3,3'-dimethoxydiphenyl-4,4'-diamine.

Examples of the aralkyl amine include aralkyl primary monoamines such as benzylamine; aralkyl primary diamines such as 1,3-bis(aminomethyl)benzene, 1,4-bis(aminomethyl)benzene, 1,3-tetramethylxylylenediamine (1,3-di(2-amino-2-methylethyl)benzene) and 1,4-tetramethylxylylenediamine (1,4-bis(2-amino-2-methylethyl)benzene).

In the above formula (1), examples of the functional group that may be substituted in $R^1$ include a nitro group, a hydroxyl group, a mercapto group, an oxo group, a thioxo group, a cyano group, a carboxy group, alkoxy-carbonyl group (e.g., an alkoxycarbonyl group having 2 to 4 total carbon atoms such as a methoxycarbonyl group and an ethoxycarbonyl group), a sulfo group, a halogen atom (e.g., fluorine, chlorine, bromine, iodine, etc.), a lower alkoxy group (e.g., a methoxy group, an ethoxy group, a propoxy group, a butoxy group, an iso-butoxy group, a sec-butoxy group, a tert-butoxy group, etc.), an aryloxy group (e.g., a phenoxy group etc.), a halogenophenoxy group (e.g., o-, m- or p-chlorophenoxy group, o-, m-, or p-bromophenoxy group, etc.), a lower alkylthio group (e.g., a methylthio group, an ethylthio group, an n-propylthio group, an iso-propylthio group, n-butylthio group, a tert-butylthio group, etc.), an arylthio group (e.g., phenylthio group etc.), a lower alkyl sulfinyl group (e.g., a methyl sulfinyl group, an ethyl sulfinyl group, etc.), a lower alkyl sulfonyl group (e.g., a methylsulfonyl group, an ethylsulfonyl group, etc.), an aryl sulfonyl group (e.g., phenyl slufonyl, etc.), a lower acyl group (e.g., a formyl group, an acetyl group, etc.), and an arylcarbonyl group (e.g., benzoyl group, etc.).

In the above formula (1), these functional groups may be multiply substituted in $R^1$. When the functional groups are multiply substituted in $R^1$, the functional groups may be the same or different from each other.

In the above formula (1), l represents an integer of 1 to 6, preferably, 1 or 2, preferably, 2.

These primary amines can be used alone or in combination of two or more kinds.

As the primary amine, in the above formula (1), a primary amine in which $R^1$ is an aromatic ring-containing hydrocarbon group having 6 to 15 total carbon atoms is preferable, or more specifically, an aromatic amine having 6 to 15 total carbon atoms and an aralkyl amine having 6 to 15 total carbon atoms are preferable.

Further, as the primary amine, those industrially used as raw materials for producing isocyanates are preferable, and examples of the primary amine include 1,5-diaminopentane (1,5-pentamethylenediamine), 1,6-diaminohexane, isophoronediamine, 1,3-bis(aminomethyl)cyclohexane, 1,4-bis(aminomethyl)cyclohexane, 4,4'-methylenebis (cyclohexylamine), 2,5-bis(aminomethyl)bicyclo[2,2,1] heptane, 2,6-bis(aminomethyl)bicyclo[2,2,1]heptane, 2,4-tolylenediamine, 2,6-tolylenediamine, 4,4'-diphenylmethanediamine, 2,4'-diphenylmethanediamine, 2,2'-diphenylmethanediamine, naphthylene-1,5-diamine, 1,3-bis(aminomethyl)benzene, 1,4-bis(aminomethyl)benzene, 1,3-tetramethylxylylenediamine, and 1,4-tetramethylxylylenediamine. In particular, 1,5-diaminopentane(1,5-pentamethylenediamine), 2,4-tolylenediamine, 2,6-tolylenediamine, 4,4'-diphenylmethanediamine, 2,4'-diphenylmethanediamine, 2,2'-diphenylmethanediamine, naphthylene-1,5-diamine, 1,3-bis(aminomethyl)benzene, 1,4-bis(aminomethyl)benzene, 1,3-tetramethylxylylenediamine, and 1,4-tetramethylxylylenediamine are preferable.

The N-unsubstituted carbamate used in the present invention is a carbamic acid ester in which a nitrogen atom in a carbamoyl group is not substituted with a functional group (i.e., nitrogen atom is bonded to two hydrogen atoms and to one carbon atom), and is represented, for example, by the following general formula (2):

$$R^2O\text{—}CO\text{—}NH_2 \qquad (2)$$

(wherein $R^2$ represents an aliphatic hydrocarbon group having 1 to 16 total carbon atoms, or an aromatic hydrocarbon group having 6 to 16 total carbon atoms.)

In the above formula (2), examples of the aliphatic hydrocarbon group having 1 to 16 total carbon atoms represented by $R^2$ include alkyl groups having 1 to 16 total carbon atoms.

Examples of the alkyl group include methyl, ethyl, propyl, iso-propyl, butyl, iso-butyl, sec-butyl, tert-butyl, pentyl, iso-pentyl, sec-pentyl, hexyl, heptyl, octyl, 2-ethylhexyl, nonyl, decyl, isodecyl, dodecyl, tetradecyl, and hexadecyl.

In the above formula (2), examples of the N-unsubstituted carbamate whose $R^2$ is an aliphatic hydrocarbon group having 1 to 16 total carbon atoms include methyl carbamate, ethyl carbamate, propyl carbamate, iso-propyl carbamate, butyl carbamate, iso-butyl carbamate, sec-butyl carbamate, tert-butyl carbamate, pentyl carbamate, iso-pentyl carbamate, sec-pentyl carbamate, hexyl carbamate, heptyl carbamate, octyl carbamate, 2-ethylhexyl carbamate, nonyl carbamate, decyl carbamate, isodecyl carbamate, dodecyl carbamate, tetradecyl carbamate, and hexadecyl carbamate.

In the above formula (2), examples of the aromatic hydrocarbon group having 6 to 16 total carbon atoms represented by $R^2$ include aryl groups having 6 to 16 total carbon atoms.

Examples of the aryl group include phenyl, tolyl, xylyl, biphenyl, naphthyl, anthryl, and phenanthryl.

In the above formula (2), examples of the N-unsubstituted carbamate in which $R^2$ is an aromatic hydrocarbon group having 6 to 16 total carbon atoms include phenyl carbamate, tolyl carbamate, xylyl carbamate, biphenyl carbamate, naphthyl carbamate, anthryl carbamate, and phenanthryl carbamate.

These N-unsubstituted carbamates can be used alone or in combination of two or more kinds.

As the N-unsubstituted carbamate, in the above formula (2), an N-unsubstituted carbamate in which $R^2$ is an aliphatic hydrocarbon group having 1 to 16 total carbon atoms is preferable, or an N-unsubstituted carbamate in which $R^2$ is an aliphatic hydrocarbon group having 2 to 12 total carbon atoms are more preferable.

The alcohol used in the present invention is, for example, a primary, secondary, or tertiary monohydric alcohol and is represented, for example, by the following formula (3):

$$R^3\text{—OH} \tag{3}$$

(wherein $R^3$ represents an aliphatic hydrocarbon group having 1 to 16 total carbon atoms, or an aromatic hydrocarbon group having 6 to 16 total carbon atoms.)

In the above formula (3), examples of the aliphatic hydrocarbon group having 1 to 16 total carbon atoms represented by $R^3$ include the alkyl groups mentioned above.

In the above formula (3), examples of the alcohol in which $R^3$ is an aliphatic hydrocarbon group having 1 to 16 total carbon atoms include methanol, ethanol, propanol, iso-propanol, butanol, iso-butanol, sec-butanol, tert-butanol, pentanol, iso-pentanol, sec-pentanol, hexanol, heptanol, octanol (1-octanol), 2-ethylhexanol, nonanol, decanol, isodecanol, dodecanol, tetradecanol, and hexadecanol.

In the above formula (3), examples of the aromatic hydrocarbon group having 6 to 16 total carbon atoms represented by $R^3$ include the aryl groups mentioned above.

In the above formula (3), examples of the alcohol in which $R^3$ is an aromatic hydrocarbon group having 6 to 16 total carbon atoms include phenol, hydroxytoluene, hydroxyxylene, biphenyl alcohol, naphthalenol, anthracenol, and phenanthrenol.

These alcohols can be used alone or in combination of two or more kinds.

As the alcohol, in the above formula (3), an alcohol in which $R^3$ is an aliphatic hydrocarbon group having 1 to 16 carbon atoms is preferable, or an alcohol in which $R^3$ is an aliphatic hydrocarbon group having 2 to 12 carbon atoms is more preferable.

The catalyst used in the present invention is a compound containing a noncoordinating anion and a metal atom, and is represented, for example, by the following formula (4):

$$MX^1{}_m X^2{}_{n-m} \tag{4}$$

(wherein M represents a metal atom belonging to Groups 1 to 16 of the Periodic Table; $X^1$ represents a noncoordinating anion; $X^2$ represents a ligand; m represents an integer of 1 to n; and n represents a valence of M.)

In the above formula (4), examples of M include metal atoms belonging to Groups 1 to 16 of the Periodic Table (according to the IUPAC Periodic Table of the Elements (version date 22 Jun. 2007); the same applies to the following).

As the metal atom, metal atoms belonging to Groups 4 and 11 to 14 of the Periodic Table are preferable, or metal atoms belonging to Group 4 and 12 of the Periodic Table are more preferable.

In addition, as the metal atom, among the above-mentioned metal atoms, those belonging to the Third to the Sixth Periods of the Periodic Table are preferable, or those belonging to the Fourth to the Sixth Periods of the Periodic Table are preferable.

More specifically, examples of the metal atom include titanium, zirconium, and hafnium (hereinabove, Group 4 of the Fourth to the Sixth Periods of the Periodic Table); copper, silver, and gold (hereinabove, Group 11 of the Fourth to the Sixth Periods of the Periodic Table); zinc, cadmium, and mercury (hereinabove, Group 12 of the Fourth to the Sixth Periods of the Periodic Table); aluminum, gallium, indium, and thallium (hereinabove, Group 13 of the Third to the Sixth Periods of the Periodic Table); and tin and lead (hereinabove, Group 14 of the Fifth to the Sixth Periods of the Periodic Table).

As the metal atom, titanium, zirconium, and hafnium (hereinabove, Group 4 of the Fourth to the Sixth Periods of the Periodic Table), and zinc, cadmium, and mercury (hereinabove, Group 12 of the Fourth to the Sixth Periods of the Periodic Table) are preferable, or titanium, hafnium, and zinc are more preferable.

In the above formula (4), the noncoordinating anion represented by $X^1$ is defined as an anion that does not coordinate to the cation to be described later or that coordinates weakly enough to be displaced by a neutral Lewis base.

Examples of the noncoordinating anion include sulfur-containing anion, oxygen-containing anion, boron-containing anion, and phosphorus-containing anion, which are noncoordinating.

Examples of the sulfur-containing anion include noncoordinating anion represented, for example, by the following general formula (5):

$$R^4SO_3{}^- \tag{5}$$

(wherein $R^4$ represents a substituent having a substituent constant σ ranging from −0.1 to +0.7.)

In the above-mentioned formula (5), the substituent constant σ is a constant that indicates the intensity of the electron attracting property of a substituent, the constant being extended from the Hammett's substituent constant and defined by Charton (see Charton, M. Prog. Phys. Org, Chem. 1981, 13, 119.), and is a dimensionless numerical value inherent in the substituent.

Examples of the substituent $R^4$ having a substituent constant σ value ranging from −0.1 to +0.7 include $CH_3$—, $C_2H_5$—, $C_3H_7$—, iso-$C_3H_7$—, $C_4H_9$—, iso-$C_4H_9$—, sec-$C_4H_9$—, tert-$C_4H_9$—, iso-$C_5H_{11}$—, sec-$C_5H_{11}$—, $C_6H_{13}$—, $C_7H_{15}$—, $C_8H_{17}$—, $C_9H_{19}$—, $C_{10}H_{21}$—, $C_{11}H_{23}$—, $C_{12}H_{25}$—, $C_{13}H_{27}$—, $C_{14}H_{29}$—, $C_{15}H_{31}$—, $C_{16}H_{33}$—, $C_6H_5$—, 2-$(CH_3)C_6H_4$—, 3-$(CH_3)C_6H_4$—, 4-$(CH_3)C_6H_4$—, 2,3-$(CH_3)_2C_6H_3$—, 2,4-$(CH_3)_2C_6H_3$—, 2,5-$(CH_3)_2C_6H_3$—, 2,6-$(CH_3)_2C_6H_3$—, 3,4-$(CH_3)_2C_6H_3$—, 3,5-$(CH_3)_2C_6H_3$—, and 3,6-$(CH_3)_2C_6H_3$—.

As the substituent $R^4$ having a substituent constant σ value ranging from −0.1 to +0.7, an aliphatic hydrocarbon group having 1 to 16 total carbon atoms or an aromatic hydrocarbon group having 6 to 16 total carbon atoms, which contain at least one fluorine atom in the above-mentioned substituent $R^4$, is preferable, and examples thereof include $CH_2F$—, $CHF_2$—, $CF_3$—, $CH_2FCH_2$—, $CHF_2CH_2$—, $CF_3CH_2$—, $CH_3CHF$—, $CH_3CF_2$—, $CH_2FCHF$—, $CHF_2CHF$—, $CF_3CHF$—, $CH_2FCF_2$—, $CHF_2CF_2$—, $C_2F_5$—, $C_3F_7$—, $C_4F_9$—, iso-$C_4F_9$—, sec-$C_4F_9$—, tert-$C_4F_9$—, $C_5F_{11}$—, iso-$C_5F_{11}$—, sec-$C_5F_{11}$—, $C_6F_{13}$—, $C_7F_{15}$—, $C_8F_{17}$—, $C_9F_{19}$—, $C_{10}F_{21}$—, $C_{11}F_{23}$—, $C_{12}F_{25}$—, $C_{13}F_{27}$—, $C_{14}F_{29}$—, $C_{15}F_{31}$—, $C_{16}F_{33}$—, 2-F—$C_6H_4$—, 3-F—$C_6H_4$—, $C_6F_5$—, 2-$(CF_3)C_6H_4$—, 3-$(CF_3)C_6H_4$—, 4-$(CF_3)C_6H_4$—, 2,3-$(CF_3)_2C_6H_3$—, 2,4-$(CF_3)_2C_6H_3$—, 2,5-$(CF_3)_2$ $C_6H_3$—, 2,6-$(CF_3)_2C_6H_3$—, 3,4-$(CF_3)_2C_6H_3$—, 3,5-$(CF_3)_2C_6H_3$—, and 3,6-$(CF_3)_2C_6H_3$—.

More specifically, examples of the sulfur-containing anion include perfluoroalkyl sulfonate anion (e.g., $OSO_2CF_3^-$ (hereinafter abbreviated as OTf⁻ in some cases), $OSO_2C_2F_5^-$, $OSO_2C_3F_7^-$, and $OSO_2C_4F_9^-$); and arylsulfonate anion ($OSO_2C_6H_4$—$CH_3^-$ and $OSO_2C_6H_5^-$).

Examples of the oxygen-containing anion include perchlorate anion ($ClO_4^-$).

Examples of the phosphorus-containing anion include hexafluorophosphate anion ($PF_6^-$).

Examples of the boron-containing anion include tetrafluoroborate anion ($BF_4^-$), tetraphenylborate anion, tetra(p-tolyl)borate anion, tetra(o-tolyl)borate anion, tetrakis(o,p-dimethylphenyl)borate anion, tetrakis(m,m-dimethylphenyl)borate anion, tetrakis[p-(trifluoromethyl)phenyl]borate anion, tetrakis(pentafluorophenyl)borate ($B(C_6F_5)_4$) anion, and tetrakis[3,5-bis(trifluoromethyl)phenyl]borate anion ($B[3,5-(CF_3)_2C_6H_3]_4^-$).

Among them, as the noncoordinating anion, perfluoroalkyl sulfonate anion, aryl sulfonate anion, hexafluorophosphate anion, tetrafluoroborate anion, tetrakis (pentafluorophenyl) borate anion, tetrakis[3,5-bis(trifluoromethyl)phenyl]borate anion are preferable, or perfluoroalkylsulfonate anion is more preferable.

In the above-mentioned formula (4), the ligand represented by $X^2$ is an atomic group that coordinates to the metal atoms mentioned above, and more specifically, examples thereof include alkyl groups (e.g., $CH_3$—, $C_2H_5$—, $C_3H_7$—, iso-$C_3H_7$—, $C_4H_9$—, iso-$C_4H_9$—, sec-$C_4H_9$—, tert-$C_4H_9$—, and $C_5H_{11}$—); alkoxy groups (e.g., $CH_3O$—, $C_2H_5O$—, $C_3H_7O$—, iso-$C_3H_7O$—, $C_4H_9O$—, iso-$C_4H_9O$—, sec-$C_4H_9O$—, tert-$C_4H_9O$—, and $C_5H_{11}O$—); amino groups ($NH_2$—); secondary amino groups (e.g., $CH_3NH$—, $C_2H_5NH$—, $C_3H_7NH$—, iso-$C_3H_7NH$—, $C_4H_9NH$—, iso-$C_4H_9NH$—, sec-$C_4H_9NH$—, tert-$C_4H_9NH$—, and $C_5H_{11}NH$—); tertiary amino groups (e.g., $(CH_3)_2N$—, $(C_2H_5)_2N$—, $(C_3H_7)_2N$—, $(C_4H_9)_2N$—, and $(C_5H_{11})_2N$—); acyloxy groups (e.g., $CH_3COO$—, $C_2H_5COO$—, $C_3H_7COO$—, iso-$C_3H_7COO$—, $C_4H_9COO$—, iso-$C_4H_9COO$—, sec-$C_4H_9COO$—, tert-$C_4H_9COO$—, $C_5H_{11}COO$—, $C_6H_{13}COO$—, $C_7H_{15}COO$—, $C_8H_{17}COO$—, $C_9H_{19}COO$—, $C_{10}H_{21}COO$—, $C_{11}H_{23}COO$—, $C_{12}H_{25}COO$—, $C_{13}H_{27}COO$—, $C_{14}H_{29}COO$—, $C_{15}H_{31}COO$—, $C_{116}H_{33}COO$—, $C_{17}H_{35}COO$—, $C_{18}H_{37}COO$—, and $C_6H_5COO$—); acetylacetonate; halogen atoms (e.g., fluorine, chlorine, bromine, and iodine); sulfate ions ($SO_4^{2-}$); oxide ions ($O_2^-$); and amide ligands (e.g., $[N(SiMe_3)_2]$).

In the above formula (4), m represents an integer of 1 to n; and n represents a valence of M.

In the above formula (4), when m is two or more (i.e., when $X^1$ is two or more per M), the respective $X^1$ may be the same or different from each other.

Further, in the above formula (4), when n−m is two or more (i.e., when $X^2$ is two or more per M), the respective $X^2$ may be the same or different from each other.

In the above formula (4), when m=n, (when the valence of M and the number of $X^1$ are the same), the compound of the above-mentioned formula (4) is formed from a cation of a metal atom (M) and a noncoordinating anion ($X^1$) without containing a ligand ($X^2$).

More specifically, examples of the compound include $Zn(OSO_2CF_3)_2$ (also known as $Zn(OTf)_2$, zinc trifluoromethanesulfonate), $Zn(OSO_2C_2F_5)_2$, $Zn(OSO_2C_3F_7)_2$, $Zn(OSO_2C_4F_9)_2$, $Zn(OSO_2C_6H_4CH_3)_2$ (zinc paratoluenesulfonate), $Zn(OSO_2C_6H_5)_2$, $Zn(BF_4)_2$, $Zn(PF_6)_2$, $Hf(OTf)_4$ (hafnium trifluoromethanesulfonate), $Sn(OTf)_2$, $Al(OTf)_3$, and $Cu(OTf)_2$.

In the above formula (4), when m<n (when the number of $X^1$ is less than the valence of M), the compound of the above-mentioned formula (4) is formed from a metal atom (M), a noncoordinating anion ($X^1$), and a ligand ($X^2$).

In such case, the compound of the above-mentioned formula (4) is formed as a compound having 1 to (n−1) ligands ($X^2$) per metal atom (M) having a valence of n. Specifically, for example, when the valence of the metal atom (M) is 4, the compound of the above-mentioned formula (4) has 1 to 3 ligands ($X^2$).

When m<n, in the compound of the above-mentioned formula (4), the cation electrically drawing a noncoordinating anion ($X^1$) is formed from the metal atom (M) and the ligand ($X^2$) coordinated thereto.

Specifically, when m<n, the compound of the above-mentioned formula (4) is formed from the cation (e.g., complex ion, etc.) formed by coordinating a ligand ($X^2$) to a metal atom (M), and a noncoordinating anion ($X^1$).

Such compound can be formed, for example, by mixing a metallic compound and a compound which forms a noncoordinating anion.

More specifically, the compound can be formed, for example, by mixing a metallic compound ($MX^2n$) made of a metal atom (M) having n ligand(s) ($X^2$) coordinated thereto, and a compound (e.g., a compound ($HX^1$) forming a noncoordinating anion as a conjugate base) which forms a noncoordinating anion ($X^1$).

Specifically, when the metallic compound ($MX^2n$) and the compound (e.g., $HX^1$, etc.) which forms a noncoordinating anion are mixed in, for example, water, an organic solvent, or the like, a portion of the ligand ($X^2$) in the metallic compound ($MX^2n$) and a noncoordinating anion ($X^1$) are substituted each other in the mixture, so that the compound of the above-mentioned formula (4) is formed.

More specifically, for example, titanium tetrachloride ($TiCl_4$) and trifluoromethanesulfonic acid ($HOSO_2CF_3$) are mixed whereby a portion of the chloride anion (Cl⁻) in the titanium tetrachloride and a triflate anion (noncoordinating anion, $OSO_2CF_3^-$) are substituted each other, so that a compound in which 1 to 3 triflate anions and chloride anions are substituted each other such as $TiCl(OTf)_3$, $TiCl_2(OTf)_2$, or $TiCl_3(OTf)$ is formed as the compound of the above-mentioned formula (4).

In the mixture, all the ligands ($X^2$) in the metallic compound ($MX^2n$) and the noncoordinating anion ($X^1$) are substituted, so that a compound having n noncoordinating anion(s) ($X^1$) may be formed in some cases.

As the compound of the above-mentioned formula (4), $Zn(OSO_2CF_3)_2$ (zinc trifluoromethanesulfonate), $Zn(OSO_2C_6H_4CH_3)_2$ (zinc paratoluenesulfonate), $Hf(OTf)_4$ (hafnium trifluoromethanesulfonate), a mixture ($TiCl(OTf)_3$, $TiCl_2(OTf)_2$, and $TiCl_3(OTf)$) of titanium tetrachloride ($TiCl_4$) and trifluoromethanesulfonic acid ($HOSO_2CF_3$) are preferable.

These compounds can be used alone or in combination of two or more kinds.

In the method for producing urethane compounds of the present invention, the primary amine, urea and/or N-unsubstituted carbamate, and alcohol as described above are mixed and the mixture is allowed to react in the presence of the above-mentioned catalyst, preferably in a liquid phase.

The amounts of the primary amine, urea and/or N-unsubstituted carbamate, and alcohol are not particularly limited and can be appropriately selected over a relatively wide range.

Usually, the amounts of the urea and N-unsubstituted carbamate, and the amount of the alcohol may be equimolar or more to the amino group in the primary amine, and therefore, the urea and/or the above-mentioned N-unsubstituted carbamate, and the alcohol themselves can also be used as reaction solvents in this reaction.

When the urea and/or the above-mentioned N-unsubstituted carbamate and the alcohol also serve as the reaction solvents, excess amounts of the urea and/or the above-mentioned N-unsubstituted carbamate and the alcohol are used as required. Large excess amounts thereof, however, increase consumption energy in the separation process after the reaction, which may be unsuitable for industrial production.

Therefore, from the viewpoint of improving the yield of the urethane compound, the amount(s) of the urea and/or the above-mentioned N-unsubstituted carbamate is/are of the order of 0.5 to 20 times moles, preferably 1 to 10 times moles, or more preferably 1 to 5 times moles with respect to one amino group of the primary amine, and the amount of the alcohol is of the order of 0.5 to 100 times moles, preferably 1 to 20 times moles, or more preferably 1 to 10 times moles, with respect to one amino group of the primary amine.

The amount of the catalyst is in the range of, for example, 0.000001 to 0.1 mol, or preferably 0.00005 to 0.05 mol, based on 1 mol of the primary amine. Even if the amount of the catalyst is more than the above range, no further remarkable reaction enhancing effect is observed, but cost may increase due to an increase in the amount. On the other hand, when the amount is less than the above range, the reaction enhancing effect may not be obtained.

The method for adding the catalyst is not particularly limited, and the method of each of package addition, continuous addition, and intermittent addition in portions does not affect the reaction activity.

In this reaction, although a reaction solvent is not necessarily required, for example, when reaction raw materials are solid or when a reaction product is deposited, blending of the reaction solvent can improve operability.

Such reaction solvent is not particularly limited as long as it is inert to or has poor reactivity to the primary amine, urea and/or N-unsubstituted carbamate, and alcohol, which are reaction raw materials, and to the urethane compound which is a reaction product, and examples thereof include aliphatic hydrocarbons (e.g., hexane, pentane, petroleum ether, ligroin, cyclododecane, and decalins); aromatic hydrocarbons (e.g., benzene, toluene, xylene, ethylbenzene, isopropylbenzene, butylbenzene, cyclohexylbenzene, tetralin, chlorobenzene, o-dichlorobenzene, methylnaphthalene, chloronaphthalene, dibenzyltoluene, triphenylmethane, phenylnaphthalene, biphenyl, diethylbiphenyl, and triethylbiphenyl); ethers (e.g., diethyl ether, diisopropyl ether, dibutyl ether, anisole, diphenyl ether, tetrahydrofuran, ethylene glycol dimethyl ether, ethylene glycol diethyl ether, ethylene glycol dibutyl ether, diethylene glycol dimethyl ether, and diethylene glycol diethyl ether); nitriles (e.g., acetonitrile, propionitrile, adiponitrile, and benzonitrile); aliphatic halogenated hydrocarbons (e.g., methylene chloride, chloroform, 1,2-dichloroethane, 1,2-dichloropropane, 1,4-dichlorobutane, etc.); amides (e.g., dimethylformamide and dimethylacetamide); nitro compounds (e.g., nitromethane and nitrobenzene); N-methylpyrrolidinone, N,N-dimethylimidazolidinone, and dimethyl sulfoxide.

Among these reaction solvents, aliphatic hydrocarbons and aromatic hydrocarbons are preferably used in consideration of economical efficiency, operability, or the like. These reaction solvents can be used alone or in combination of two or more kinds.

The amount of the reaction solvent is not particularly limited as long as it is sufficient for the urethane compound as a desired product to be dissolved. Industrially, the amount of the reaction solvent is preferably minimized as much as possible in view that since it is necessary to recover the reaction solvent from the reaction solution, the energy consumed for the recovery can be reduced as much as possible, and in view that a large amount of the reaction solvent can decrease substrate concentration on the reaction to slow the reaction rate. More specifically, the amount of the reaction solvent is usually in the range of 0.1 to 500 parts by mass, or preferably 1 to 100 parts by mass, per 1 part by mass of the primary amine.

In this reaction, the reaction temperature is appropriately selected from the range of 100 to 350° C., or preferably 150 to 300° C. When the reaction temperature is lower than this range, the reaction rate may decrease. On the other hand, when it is higher than this range, a side reaction increases, so that the yield of the urethane compound as a desired product may be reduced.

The reaction is usually carried out under atmospheric pressure. However, when the boiling point of the component in the reaction solution is lower than the reaction temperature, the reaction may be carried out under an increased pressure or, if necessary, under a reduced pressure.

The reaction time is in the range of, for example, 0.1 to 20 hours, or preferably 0.5 to 10 hours. When the reaction time is shorter than this range, the yield of the urethane compound as a desired product may be reduced. On the other hand, when it is longer than this range, the reaction is unsuitable for industrial production.

Then, this reaction may be carried out, for example, by charging a primary amine, a urea and/or an N-unsubstituted carbamate, an alcohol, a catalyst, and if necessary, a reaction solvent, in a reaction vessel under the above-mentioned conditions, and stirring or mixing the charged mixture. This produces a urethane compound as a desired product represented, for example, by the following general formula (6) under a mild condition at low cost and high yield for a short period of time.

$(R^3OCONH)$-$R^1$ (6)

(wherein $R^1$ is defined as $R^1$ in the above-mentioned formula (1); $R^3$ is defined as $R^3$ in the above-mentioned formula (3); and 1 is defined as 1 in the above-mentioned formula (1).)

In this reaction, ammonia is secondarily produced.

Further, in this reaction, when an N-unsubstituted carbamate is blended, alcohol represented, for example, by the following general formula (7) is secondarily produced:

$R^2$—OH (7)

(wherein $R^2$ is defined as $R^2$ in the above-mentioned formula (2).)

In this reaction, either of a batch reaction process and a continuous reaction process can be adopted.

The reaction is carried out preferably while the secondarily produced ammonia was distilled out of the system. Further, when an N-unsubstituted carbamate is blended, the reaction is carried out while the secondarily produced alcohol was distilled out of the system.

Thus, the production of the urethane compound as a desired product can be accelerated to further improve the yield.

When the urethane compound thus obtained is isolated, the urethane compound may be separated from the reaction solution containing, for example, excess (unreacted) urea and/or N-unsubstituted carbamate, excess (unreacted) alcohol, catalyst, urethane compound, reaction solvent, secondarily produced ammonia, and optionally, secondarily produced alcohol by a known separation and purification method.

According to the method for producing urethane compounds, the urethane compound can be produced at low cost and high yield for a short period of time by a simple process. Therefore, the present invention can be suitably used as an industrial method for producing urethane compounds.

The present invention includes a method for producing isocyanates in which the urethane compound obtained by the above-mentioned urethane compound producing method is thermally decomposed to produce isocyanates.

Specifically, in the method for producing isocyanates, the urethane compound obtained by the above-mentioned urethane compound producing method is thermally decomposed to produce an isocyanate represented by the following general formula (8) corresponding to the above-mentioned primary amine,

$$R^1-(NCO)_l \tag{8}$$

(wherein $R^1$ is defined as $R^1$ in the above-mentioned formula (1), and l is defined as l in the above-mentioned formula (1).) and an alcohol, which is by-product, represented by the following general formula (9):

$$R^3-OH \tag{9}$$

(wherein $R^3$ is defined as $R^3$ in the above-mentioned formula (3).)

No particular limitation is imposed on the thermal decomposition. Known decomposition methods such as a liquid phase method and a vapor phase method can be used.

In the vapor phase method, the isocyanate and alcohol produced by the thermal decomposition can be separated from a gaseous product mixture by fractional condensation. In the liquid phase method, the isocyanate and alcohol produced by the thermal decomposition can be separated, for example, by distillation or using a solvent and/or inert gas as a support substance.

As the thermal decomposition, a liquid phase method is preferable from the viewpoint of workability.

Since the thermal decomposition reaction of the urethane compound in the liquid phase method is a reversible reaction, preferably, the urethane compound is thermally decomposed while the isocyanate represented by the above-mentioned general formula (8) and/or the alcohol represented by the above-mentioned general formula (9) are drawn out of the reaction mixture, for example, in the form of vapors and then separated, in order to suppress a reverse reaction to the thermal decomposition reaction (i.e., the urethane-forming reaction between the isocyanate represented by the above-mentioned general formula (8) and the alcohol represented by the above-mentioned general formula (9)).

As the reaction condition of the thermal decomposition reaction, preferable are conditions such that the urethane compound can be thermally decomposed in an excellent manner, and the isocyanate (the above-mentioned general formula (8)) and alcohol (the above-mentioned general formula (9)) produced by the thermal decomposition process evaporate, whereby the carbamate and the isocyanate fail to reach equilibrium, and further, a side reaction such as polymerization of isocyanates is suppressed.

As the reaction conditions, more specifically, the thermal decomposition temperature is usually 350° C. or lower, preferably from 80 to 350° C., or more preferably from 100 to 300° C. At the thermal decomposition temperature lower than 80° C., a practical reaction rate may not be obtained. On the other hand, at the thermal decomposition temperature higher than 350° C., an undesired side reaction such as polymerization of isocyanates may occur. It is preferable that the pressure during the thermal decomposition reaction is a pressure for allowing the alcohol produced to be vaporized at the thermal decomposition reaction temperature specified above. For practical use, the pressure is preferably in the range of 0.133 to 90 kPa in terms of equipment and utilities.

Although purified urethane compound can be used for the thermal decomposition, the crude material of the urethane compound obtained by the recovery and separation of excess (unreacted) urea and/or N-unsubstituted carbamate, excess (unreacted) alcohol, catalyst, reaction solvent, secondarily produced ammonia, and alcohol, optionally, produced secondarily may be used to continue the thermal decomposition after completion of the above-mentioned reaction (i.e., reaction of the primary amine, the urea and/or the N-unsubstituted carbamate, and the alcohol).

Further, if necessary, a catalyst and an inert solvent may be added. Although the catalyst and the inert solvent vary depending on their kinds, they may be added at any timing of during the above-mentioned reaction, before and after distillation and separation after the reaction, and before and after separation of the urethane compound.

As the catalyst used for the thermal decomposition, at least one metal selected from the group consisting of Sn, Sb, Fe, Co, Ni, Cu, Cr, Ti, Pb, Mo, and Mn, or a compound thereof such as oxide, halide, carboxylate, phosphate, and organometallic compound, used for the urethane-forming reaction of an isocyanate and a hydroxyl group is used. Among them, Fe, Sn, Co, Sb, and Mn are preferably used in the thermal decomposition because they exhibit the effect of suppressing the production of by-product.

Examples of the metallic catalyst of Sn include tin oxide, tin chloride, tin bromide, tin iodide, tin formate, tin acetate, tin oxalate, tin octylate, tin stearate, tin oleate, tin phosphorate, dibutyltin dichloride, dibutyltin dilaurate, and 1,1,3,3-tetrabutyl-1,3-dilauryloxydistannoxane.

Examples of the metallic catalysts of Fe, Co, Sb, and Mn include acetate, benzoate, naphthenate, and acetylacetonate thereof.

The amount of the catalyst is in the range of 0.0001 to 5% by mass, or preferably 0.001 to 1% by mass, per the reaction solution, as a metal or a compound thereof.

The inert solvent is not particularly limited as long as it dissolves at least the urethane compound, is inert to the urethane compound and the isocyanate, and is stable at the thermal decomposition temperature. For efficient thermal decomposition reaction, the inert solvent preferably has a higher boiling point than the isocyanate to be produced. Examples of the inert solvent include esters such as dioctyl phthalate, didecyl phthalate, and didodecyl phthalate; and aromatic hydrocarbons or aliphatic hydrocarbons regularly used as heat transfer medium such as dibenzyltoluene, triphenylmethane, phenylnaphthalene, biphenyl, diethylbiphenyl, and triethylbiphenyl.

The inert solvent is available as a commercially available product and examples thereof include Barrel Process Oil B-01 (aromatic hydrocarbon, boiling point: 176° C.), Barrel Process Oil B-03 (aromatic hydrocarbon, boiling point: 280° C.), Barrel Process Oil B-04AB (aromatic hydrocarbon, boiling point: 294° C.), Barrel Process Oil B-05 (aromatic hydrocarbon, boiling point: 302° C.), Barrel Process Oil B-27 (aromatic hydrocarbon, boiling point: 380° C.), Barrel Process Oil B-28AN (aromatic hydrocarbon, boiling point: 430° C.), Barrel Process Oil B-30 (aromatic hydrocarbon, boiling point: 380° C.), Barrel Therm 200 (aromatic hydrocarbon, boiling point: 382° C.), Barrel Therm 300 (aromatic hydrocarbon, boiling point: 344° C.), Barrel Therm 400 (aromatic hydrocarbon, boiling point: 390° C.), Barrel Therm 1H (aromatic hydrocarbon, boiling point: 215° C.), Barrel Therm 21-1 (aromatic hydrocarbon, boiling point: 294° C.), Barrel Therm 350 (aromatic hydrocarbon, boiling point: 302° C.), Barrel Therm 470 (aromatic hydrocarbon, boiling point: 310° C.), Barrel Therm PA (aromatic hydrocarbon, boiling point: 176° C.), Barrel Therm 330 (aromatic hydrocarbon, boiling point: 257° C.), and Barrel Therm 430 (aromatic hydrocarbon, boiling point: 291° C.) (hereinabove manufactured by Matsumura Oil Co., Ltd.); and NeoSK-OIL 1400 (aromatic hydrocarbon, boiling point: 391° C.), NeoSK-OIL 1300 (aromatic hydrocarbon, boiling point: 291° C.), NeoSK-OIL 330 (aromatic hydrocarbon, boiling point: 331° C.), NeoSK-OIL 170 (aromatic hydrocarbon, boiling point: 176° C.), NeoSK-OIL 240 (aromatic hydrocarbon, boiling point: 244° C.), KSK-OIL 260 (aromatic hydrocarbon, boiling point: 266° C.), and KSK-OIL 280 (aromatic hydrocarbon, boiling point: 303° C.) (hereinabove, manufactured by Soken Tecnix Co., Ltd.).

An amount of the inert solvent is in the range of 0.001 to 100 parts by mass, preferably 0.01 to 80 parts by mass, or more preferably 0.1 to 50 parts by mass, per 1 part by mass of the urethane compound.

The thermal decomposition reaction can be carried out by a batch reaction process in which the urethane compound, the catalyst, and the inert solvent are charged at one time, or by a continuous reaction process in which the urethane compound is continuously charged into the inert solvent containing the catalyst under reduced pressure.

In the thermal decomposition, an isocyanate and an alcohol are produced, and for example, allophanate, amines, urea, carbonate, carbamate, and carbon dioxide may also be produced by a side reaction in some cases. Therefore, if necessary, the isocyanate thus produced is purified by a known method.

In the thermal decomposition reaction, since isocyanates corresponding to the primary amine can be produced by thermally decomposing the urethane compound obtained above, for example, polyisocyanates industrially used as a raw material of polyurethane can be produced easily and efficiently.

In the foregoing, the method for producing urethanes and the method for producing isocyanates have been discussed. However, the production method of the present invention may include known steps, such as pre-treatment steps including a dehydration step; intermediate steps; or post-treatment steps including a purification step and a recovery step.

EXAMPLES

While in the following, the present invention will be described in further detail with reference to Examples, the present invention is not limited to any of them. In the following Examples and Comparative Examples, a liquid chromatograph (a UV detector (254 nm) and an RI detector) was used for quantification of reaction products.

Example 1

A 200 ml four-neck glass flask equipped with a thermometer and a reflux condenser was charged with zinc paratoluenesulfonate (0.204 g: 0.500 mmol) as a catalyst, and further charged with 2,4-diaminotoluene (12.2 g: 100 mmol), urea (12.0 g: 200 mmol), and 1-octanol (45.6 g: 350 mmol). While a nitrogen gas was allowed to flow at 100 ml per minute, the charged mixture was allowed to react at a reaction temperature of 180° C. for 6 hours.

When a portion of the reaction solution was sampled and quantified, it was confirmed that 2,4-bis(octyloxy carbonylamino)toluene (hereinafter abbreviated as dicarbamate (the same applies to the following Examples and Comparative Examples)) was produced at a yield of 61% by mol based on 2,4-diaminotoluene. It was also confirmed that mono(octyloxycarbonylamino)aminotluene (hereinafter abbreviated as monocarbamate (the same applies to the following Examples and Comparative Examples)) was produced at a yield of 23% by mol.

Example 2

The same operation as in Example 1 was performed except that hafnium trifluoromethanesulfonate (0.500 mmol) was charged as a catalyst in place of zinc paratoluenesulfonate.

The result of the quantitative analysis confirmed that dicarbamate was produced at a yield of 60% by mol and monocarbamate was produced at a yield of 23% by mol.

Example 3

The same operation as in Example 1 was performed except that zinc trifluoromethanesulfonate (0.500 mmol) was charged as a catalyst in place of zinc paratoluenesulfonate.

The result of the quantitative analysis confirmed that dicarbamate was produced at a yield of 65% by mol and monocarbamate was produced at a yield of 22% by mol.

Example 4

The same operation as in Example 1 was performed except that titanium tetrachloride (0.500 mmol) and trifluoromethanesulfonic acid (1.50 mmol) were charged as a catalyst in place of zinc paratoluenesulfonate.

The result of the quantitative analysis confirmed that dicarbamate was produced at a yield of 68% by mol and monocarbamate was produced at a yield of 19% by mol.

Example 5

A 200 ml four-neck glass flask equipped with a thermometer, a reflux condenser, and a stirrer was charged with zinc trifluoromethanesulfonate (0.182 g: 0.500 mmol) as a catalyst, and further charged with 2,4-diaminotoluene (12.2 g: 100 mmol), urea (18.0 g: 300 mmol), and 1-octanol (71.6 g: 550 mmol). While a nitrogen gas was allowed to flow at 100 ml per minute and stirred at 300 rpm, the charged mixture was allowed to react at a reaction temperature of 180° C. for 4 hours.

When a portion of the reaction solution was sampled and quantified, it was confirmed that dicarbamate was produced at a yield of 79% by mol based on 2,4-diaminotoluene. It was also confirmed that monocarbamate was produced at a yield of 14% by mol.

Example 6

The same operation as in Example 5 was performed except that the reaction temperature was 215° C. and the reaction time was 2 hours.

The result of the quantitative analysis confirmed that dicarbamate was produced at a yield of 96% by mol and monocarbamate was produced at a yield of 3% by mol.

Example 7

A 1-liter SUS autoclave equipped with a pressure control valve, a reflux condenser, a gas-liquid separator, and a stirrer was charged with a mixture of 2,4-diaminotoluene (76.5 g: 0.626 mol), urea (113 g: 1.87 mol), and 1-butanol (255 g: 3.44 mol), and further charged with a mixture of zinc trifluoromethanesulfonate (1.16 g: 3.14 mmol) as a catalyst and 1-butanol (23.4 g: 316 mmol). While a nitrogen gas was allowed to flow at 1 liter per minute and stirred at 500 rpm, the charged mixture was allowed to react for 4 hours while the internal pressure was controlled with the pressure control valve so that the reaction temperature was maintained at 215° C.

When a portion of the reaction solution was sampled and quantified, it was confirmed that dicarbamate (2,4-bis(butyloxycarbonylamino)toluene) was produced at a yield of 89% by mol based on 2,4-diaminotoluene. It was also confirmed that monocarbamate (mono(butyloxycarbonylamino)aminotoluene) was produced at a yield of 3% by mol.

Example 8

A 200 ml four-neck glass flask equipped with a thermometer, a reflux condenser, and a stirrer was charged with zinc trifluoromethanesulfonate (0.182 g: 0.500 mmol) as a catalyst, and further charged with 2,4-diaminotoluene (12.2 g: 100 mmol), octyl carbamate (34.7 g: 200 mmol), and 1-octanol (19.5 g: 150 mmol). While a nitrogen gas was allowed to flow at 100 ml per minute and stirred at 300 rpm, the charged mixture was allowed to react at a reaction temperature of 215° C. for 2 hours.

When a portion of the reaction solution was sampled and quantified, it was confirmed that dicarbamate was produced at a yield of 79% by mol based on 2,4-diaminotoluene. It was also confirmed that monocarbamate was produced at a yield of 9% by mol.

Example 9

A 1-liter SUS autoclave equipped with a pressure control valve, a reflux condenser, a gas-liquid separator, and a stirrer was charged with a mixture of 2,4-diaminotoluene (80.5 g: 0.660 mol), urea (113 g: 1.88 mol), and 1-butanol (298 g: 4.02 mol), and further charged with zinc paratoluenesulfonate (0.64 g: 1.56 mmol) as a catalyst. While a nitrogen gas was allowed to flow at 1 liter per minute and stirred at 500 rpm, the charged mixture was allowed to react for 8 hours while the internal pressure was controlled with the pressure control valve so that the reaction temperature was maintained at 200° C.

When a portion of the reaction solution was sampled and quantified, it was confirmed that dicarbamate was produced at a yield of 96% by mol based on 2,4-diaminotoluene. It was also confirmed that monocarbamate was produced at a yield of 0.4% by mol.

Example 10

A 1-liter SUS autoclave equipped with a pressure control valve, a reflux condenser, a gas-liquid separator, and a stirrer was charged with a mixture of 1,5-diaminopentane (51.1 g: 0.5 mol), urea (72.1 g: 1.2 mol), and 1-butanol (222.4 g: 3.0 mol), and further charged with zinc paratoluenesulfonate (1.02 g: 2.5 mmol) as a catalyst. While a nitrogen gas was allowed to flow at 0.3 L per minute and stirred at 500 rpm, the charged mixture was allowed to react for 3 hours while the internal pressure was controlled with the pressure control valve so that the reaction temperature was maintained at 215° C.

When a portion of the reaction solution was sampled and quantified, it was confirmed that dicarbamate (1,5-bis(butyloxycarbonylamino)pentane) was produced at a yield of 98% by mol based on 1,5-diaminopentane. A peak resulting from monocarbamate (mono(butyloxycarbonylamino)aminopentane) was almost no detection.

Example 11

The same operation as in Example 9 was performed except that 1,6-diaminohexane (58.1 g: 0.5 mol) was charged in place of 1,5-diaminopentane (51.1 g: 0.5 mol).

When a portion of the reaction solution was sampled and quantified, It was confirmed that dicarbamate (1,6-bis(butyloxycarbonylamino)hexane) was produced at a yield of 98% by mol based on 1,6-diaminohexane. A peak resulting from monocarbamate (mono(butyloxycarbonylamino)aminohexane) was almost no detection.

Comparative Example 1

The same operation as in Example 1 was performed except that the catalyst (zinc paratoluenesulfonate) was not charged.

The result of the quantitative analysis confirmed that dicarbamate was produced at a yield of 48% by mol and monocarbamate was produced at a yield of 27% by mol.

Comparative Example 2

The same operation as in Example 1 was performed except that zinc bromide (0.500 mmol) was changed as a catalyst in place of zinc paratoluenesulfonate.

The result of the quantitative analysis confirmed that dicarbamate was produced at a yield of 53% by mol and monocarbamate was produced at a yield of 27% by mol.

Comparative Example 3

The same operation as in Example 5 was performed except that a catalyst (zinc trifluoromethanesulfonate) was not charged.

The result of the quantitative analysis confirmed that dicarbamate was produced at a yield of 74% by mol and monocarbamate was produced at a yield of 16% by mol.

Comparative Example 4

The same operation as in Example 7 was performed except that a catalyst (zinc trifluoromethanesulfonate) was not charged and the amount of the urea was 1.88 mol.

The result of the quantitative analysis confirmed that dicarbamate was produced at a yield of 79% by mol and monocarbamate was produced at a yield of 10% by mol.

Comparative Example 5

The same operation as in Example 8 was performed except that a catalyst (zinc trifluoromethanesulfonate) was not charged.

The result of the quantitative analysis confirmed that dicarbamate was produced at a yield of 48% by mol and monocarbamate was produced at a yield of 28% by mol.

Comparative Example 6

The same operation as in Example 10 was performed except that a catalyst (zinc paratoluenesulfonate) was not charged.

The result of the quantitative analysis confirmed that dicarbamate (1,5-bis(butyloxycarbonylamino)pentane) was produced at a yield of 86% by mol. A peak resulting from monocarbamate (mono(butyloxycarbonylamino)aminopentane) was almost no detection.

Comparative Example 7

The same operation as in Example 11 was performed except that a catalyst (zinc paratoluenesulfonate) was not charged.

The result of the quantitative analysis confirmed that dicarbamate (1,6-bis(butyloxycarbonylamino)hexane) was produced at a yield of 85% by mol. A peak resulting from monocarbamate (mono(butyloxycarbonylamino)aminohexane) was almost no detection.

The blending formulation of each component in Examples 1 to 11 and Comparative Examples 1 to 7, yields of dicarbamate and monocarbamate in Examples 1 to 11 and Comparative Examples 1 to 7 are shown in Tables 1 to 4. In the tables, trace indicates that little carbamate was detected.

TABLE 1

| Synthesis of Urethane Compound | | | Ex. 1 | Ex. 2 | Ex. 3 | Ex. 4 | Ex. 5 |
|---|---|---|---|---|---|---|---|
| Blending Formulation | Catalyst | | Zinc Paratoluene-sulfonate | Hafnium Trifluoromethane-sulfonate | Zinc Trifluoromethane-sulfonate | Titanium Tetrachloride | Zinc Trifluoromethane-sulfonate |
| | | Amount Contained | 0.5 mmol | 0.5 mmol | 0.5 mmol | 0.5 mmol | 0.5 mmol |
| | | | — | — | — | Trifluoromethane-sulfonic Acid | — |
| | | Amount Contained | — | — | — | 1.5 mmol | — |
| | Primary Amine | | 2,4-diamino-toluene | 2,4-diamino-toluene | 2,4-diamino-toluene | 2,4-diamino-toluene | 2,4-diamino-toluene |
| | | Amount Contained | 100 mmol | 100 mmol | 100 mmol | 100 mmol | 100 mmol |
| | Urea | Amount Contained | 200 mmol | 200 mmol | 200 mmol | 200 mmol | 300 mmol |
| | Carbamate | | — | — | — | — | — |
| | | Amount Contained | — | — | — | — | — |
| | Alcohol | | 1-Octanol | 1-Octanol | 1-Octanol | 1-Octanol | 1-Octanol |
| | | Amount Contained | 350 mmol | 350 mmol | 350 mmol | 350 mmol | 550 mmol |
| Conditions | Reaction Temperature | | 180° C. | 180° C. | 180° C. | 180° C. | 180° C. |
| | Reaction Time | | 6 hours | 6 hours | 6 hours | 6 hours | 4 hours |
| Yield | Dicarbamate | | 61 mol % | 60 mol % | 65 mol % | 68 mol % | 79 mol % |
| | Monocarbamate | | 23 mol % | 23 mol % | 22 mol % | 19 mol % | 14 mol % |

TABLE 2

| Synthesis of Urethane Compound | | | Ex. 6 | Ex. 7 | Ex. 8 | Ex. 9 | Ex. 10 | Ex. 11 |
|---|---|---|---|---|---|---|---|---|
| Blending Formulation | Catalyst | | Zinc Trifluoro-methane-sulfonate | Zinc Trifluoro-methane-sulfonate | Zinc Trifluoro-methane-sulfonate | Zinc Paratoluene-sulfonate | Zinc Paratoluene-sulfonate | Zinc Paratoluene-sulfonate |
| | | Amount Contained | 0.5 mmol | 3.14 mmol | 0.5 mmol | 1.56 mmol | 2.5 mmol | 2.5 mmol |
| | | | — | — | — | — | — | — |
| | | Amount Contained | — | — | — | — | — | — |
| | Primary Amine | | 2,4-diamino-toluene | 2,4-diamino-toluene | 2,4-diamino-toluene | 2,4-diamino-toluene | 1,5-diamino-pentane | 1,6-diamino-hexane |
| | | Amount Contained | 100 mmol | 0.626 mol | 100 mmol | 0.660 mol | 0.5 mol | 0.5 mol |
| | Urea | Amount Contained | 300 mmol | 1.87 mol | — | 1.88 mol | 1.2 mol | 1.2 mol |
| | Carbamate | | — | — | Octyl Carbamate | — | — | — |
| | | Amount Contained | — | — | 200 mmol | — | — | — |
| | Alcohol | | 1-Octanol | 1-Butanol | 1-Octanol | 1-Butanol | 1-Butanol | 1-Butanol |
| | | Amount Contained | 550 mmol | 3.76 mol | 150 mmol | 4.02 mol | 3.0 mol | 3.0 mol |
| Conditions | Reaction Temperature | | 215° C. | 215° C. | 215° C. | 200° C. | 215° C. | 215° C. |
| | Reaction Time | | 2 hours | 4 hours | 2 hours | 8 hours | 3 hours | 3 hours |
| Yield | Dicarbamate | | 96 mol % | 89 mol % | 79 mol % | 96 mol % | 98 mol % | 98 mol % |
| | Monocarbamate | | 3 mol % | 3 mol % | 9 mol % | 0.4 mol % | trace | trace |

TABLE 3

| Synthesis of Urethane Compound | | Comp. Ex. 1 | Comp. Ex. 2 | Comp. Ex. 3 | Comp. Ex. 4 |
|---|---|---|---|---|---|
| Blending Formulation | Catalyst | — | Zinc Bromide | — | — |
| | Amount Contained | — | 0.5 mmol | — | — |
| | | — | — | — | — |
| | Amount Contained | — | — | — | — |
| | Primary Amine | 2,4-diaminotoluene | 2,4-diaminotoluene | 2,4-diaminotoluene | 2,4-diaminotoluene |
| | Amount Contained | 100 mmol | 100 mmol | 100 mmol | 0.626 mol |
| | Urea Amount Contained | 200 mmol | 200 mmol | 300 mmol | 1.88 mol |
| | Carbamate | — | — | — | — |
| | Amount Contained | — | — | — | — |
| | Alcohol | 1-Octanol | 1-Octanol | 1-Octanol | 1-Butanol |
| | Amount Contained | 350 mmol | 350 mmol | 550 mmol | 3.76 mol |
| Conditions | Reaction Temperature | 180° C. | 180° C. | 180° C. | 215° C. |
| | Reaction Time | 6 hours | 6 hours | 4 hours | 4 hours |
| Yield | Dicarbamate | 48 mol % | 53 mol % | 74 mol % | 79 mol % |
| | Mnnocarbamate | 27 mol % | 27 mol % | 16 mol % | 10 mol % |

TABLE 4

| Synthesis of Urethane Compound | | Comp. Ex. 5 | Comp. Ex. 6 | Comp. Ex. 7 |
|---|---|---|---|---|
| Blending Formulation | Catalyst | — | — | — |
| | Amount Contained | — | — | — |
| | | — | — | — |
| | Amount Contained | — | — | — |
| | Primary Amine | 2,4-diaminotoluene | 1,5-diaminopentane | 1,6-diaminohexane |
| | Amount Contained | 100 mmol | 0.5 mol | 0.5 mol |
| | Urea Amount Contained | — | 1.2 mol | 1.2 mol |
| | Carbamate | Octyl Carbamate | — | — |
| | Amount Contained | 200 mmol | — | — |
| | Alcohol | 1-Octanol | 1-Butanol | 1-Butanol |
| | Amount Contained | 150 mmol | 3.0 mol | 3.0 mol |
| Conditions | Reaction Temperature | 215° C. | 215° C. | 215° C. |
| | Reaction Time | 2 hours | 3 hours | 3 hours |
| Yield | Dicarbamate | 48 mol % | 86 mol % | 85 mol % |
| | Monocarbamate | 28 mol % | trace | trace |

Example 12

Vacuum Distillation of Light-Boiling Fraction

A 500 ml glass flask equipped with a stirrer and a condenser tube was charged with 403.3 g of the reaction solution obtained in Example 7, and while the charged mixture was stirred at 200 rpm, the pressure in the vessel was reduced to 2 kPa with a vacuum pump. The temperature in the vessel was increased to 100° C. with circulation water of 25° C. flowing through the condenser tube, so that a low-boiling fraction was distilled off and the reaction solution was condensed. Subsequently, the temperature of the circulation water was set to 70° C., and the temperature in the vessel was increased to 180° C., so that the low-boiling fraction was distilled off and the reaction solution was condensed, to finally obtain a brown concentrate in an amount of 170.00 g.

The light-boiling fraction was analyzed with a liquid chromatograph and a gas chromatograph, and the result confirmed that the light-boiling fraction primarily contained butanol and butyl carbamate, and that a compound derived from 2,4-diaminotoluene was not present.

From this result, the derivative of 0.626 mol of 2,4-diaminotoluene was considered to be present in the concentrate.

Subsequently, the above-mentioned operation was repeated over two batches to thereby obtain a brown concentrate amounting to 510 g made of a derivative of 1.88 mol of 2,4-diaminotoluene.

[Thermal Decomposition Reaction of Concentrate]

A 1-liter glass separable flask equipped with a thermometer, a stirrer, a rectifying column having a reflux tube at its upper portion, a device fitted with a vessel for feeding raw materials and a feeding pump, and a drawing-out cock at the bottom was charged with 50 g (equivalent to 0.188 mol of 2,4-diaminotoluene) of the concentrate obtained above and 116.6 g of Barrel Process Oil B-05 (manufactured by Matsumura Oil Co., Ltd.) as a solvent, and while the charged mixture was stirred at 300 rpm, the pressure in the vessel was reduced to 10 kPa with a vacuum pump. After heating was started with circulation water of 90° C. flowing through the reflux tube, the temperature at the top of the column increased around 220° C., so that tolylene diisocyanate began to condense in the reflux tube. Then, the reflux ratio was set at 5

(=reflux for 10 seconds/distillation for 2 seconds) to distill the tolylene diisocyanate off. Two hours after the start of distillation, the mixture was supplied from the vessel for feeding raw materials that was charged with 342 g (equivalent to 1.26 mol of 2,4-diaminotoluene) of the concentrate and 798 g of Barrel Process Oil B-05, to a reaction vessel at a rate of 72 g/h using the feeding pump, and the reaction was further carried out for 14 hours. During the reaction, in order to keep the liquid surface level constant in the reaction vessel, the reaction solution was drawn out from the drawing-out cock at the bottom of the flask every 2 hours from the start of the supply of the raw materials.

The amount of the reaction solution distilled became stable 7 hours after the start of distillation, so that compositions of the distillate obtained from 7 hours to 14 hours after the start of distillation and the reaction solution drawn out from the bottom were determined with a liquid chromatograph, and the molar yield of 2,4-tolylene diisocyanate to 2,4-diaminotoluene was calculated by the following formula:

> Yield of tolylene diisocyanate (mol %/diaminotoluene)=tolylene diisocyanate (mol) distilled from 7 hours to 14 hours after the start of distillation/ diaminotoluene (mol) supplied from 7 hours to 14 hours after the start of distillation–sum of 2,4-bis(butyloxycarbonylamino)toluene, mono (butyloxycarbonylamino)aminotoluene, and tolylene diisocyanate (mol) of the reaction solution drawn out from 7 hours to 14 hours after the start of distillation)

The yield of 2,4-tolylene diisocyanate to 2,4-diaminotoluene obtained by the above calculation was 84.8 mol %. The yield of 2,4-bis(butyloxycarbonylamino)toluene to 2,4-diaminotoluene in Example 7 was 89% by mol. This indicates that 95% of 2,4-bis(butyloxycarbonylamino)toluene became 2,4-tolylene diisocyanate by the thermal decomposition reaction. After completion of the carbamate-forming reaction, the thermal decomposition reaction was confirmed to be practicable only by distilling off the light-boiling fraction, without the need of eliminating or detoxifying the carbamate-forming catalyst.

Example 13

Carbamate-Forming Reaction

The same operation as in Example 7 was performed except that zinc paratoluenesulfonate (0.640 g: 1.57 mmol) was changed as a catalyst in place of zinc trifluoromethanesulfonate.

The result of the quantitative analysis confirmed that dicarbamate and monocarbamate were produced at yields of 86% by mol and 3% by mol, respectively.

[Vacuum Distillation of Light-Boiling Fraction]

A 500 ml glass flask equipped with a stirrer and a condenser tube was charged with 375 g of the reaction solution obtained by the above-mentioned carbamate-forming reaction, and while the charged mixture was stirred at 200 rpm, the pressure in the vessel was reduced to 2 kPa with a vacuum pump. The temperature in the vessel was increased to 100° C. with circulation water of 25° C. flowing through the condenser tube, so that a low-boiling fraction was distilled off and the carbamate-forming reaction solution was condensed. Subsequently, the temperature of the circulation water was set to 70° C., and the temperature in the vessel was increased to 180° C., so that the low-boiling fraction was distilled off and the carbamate-forming reaction solution was condensed, to finally obtain 193 g of a brown concentrate. The light-boiling fraction was analyzed with a liquid chromatograph and a gas chromatograph, and the result confirmed that the light-boiling fraction primarily contained butanol and butyl carbamate, and that a compound derived from 2,4-diaminotoluene was not present. From this result, the derivative of 0.626 mol of 2,4-diaminotoluene was considered to be present in the concentrate.

Subsequently, the above-mentioned operation was repeated over three batches to thereby obtain a brown concentrate amounting to 770 g made of a derivative of 2.50 mol of 2,4-diaminotoluene.

[Thermal Decomposition Reaction of Concentrate]

A 1-liter glass separable flask equipped with a thermometer, a stirrer, a rectifying column having a reflux tube at its upper portion, a device fitted with a vessel for feeding raw materials and a feeding pump, and a drawing-out cock at the bottom was charged with 100 g (equivalent to 0.32 mol of 2,4-diaminotoluene) of the concentrate obtained above and 100 g of Barrel Process Oil B-05 (manufactured by Matsumura Oil Co., Ltd.) as a solvent, and while the charged mixture was stirred at 300 rpm, the pressure in the vessel was reduced to 10 kPa with a vacuum pump. After heating was started with circulation water of 90° C. flowing through the reflux tube, the temperature at the top of the column increased around 220° C., so that tolylene diisocyanate began to condense in the reflux tube. Then, the reflux ratio was set at 5 (=reflux for 10 seconds/distillation for 2 seconds) to distill the tolylene diisocyanate off. Two hours after the start of distillation, the mixture was supplied from the vessel for feeding raw materials that was charged with 380.0 g (equivalent to 1.23 mol of 2,4-diaminotoluene) of the concentrate and 380.0 g of Barrel Process Oil B-05 to a reaction vessel at a rate of 48 g/h using the feeding pump, and the reaction was further carried out for 14 hours. During the reaction, in order to keep the liquid surface level constant in the reaction vessel, the reaction solution was drawn out from the drawing-out cock at the bottom of the flask every 2 hours from the start of the supply of the raw materials.

The amount of the reaction solution distilled became stable 6 hours after the start of distillation, so that compositions of the distillate obtained from 6 hours to 16 hours after the start of distillation and the reaction solution drawn out from the bottom were determined with a liquid chromatograph, and the molar yield of 2,4-tolylene diisocyanate to 2,4-diaminotoluene was calculated by the following formula:

> Yield of tolylene diisocyanate (mol %/diaminotoluene)=tolylene diisocyanate (mol) distilled from 6 hours to 16 hours after the start of distillation/ diaminotoluene (mol) supplied from 6 hours to 16 hours after the start of distillation sum of 2,4-bis(butyloxycarbonylamino)toluene, mono(butyloxycarbonylamino)aminotoluene, and tolylene diisocyanate (mol) of the reaction solution drawn out from 6 hours to 16 hours after the start of distillation)

The yield of 2,4-tolylene diisocyanate to 2,4-diaminotoluene obtained by the above calculation was 85.4 mol %. The yield of 2,4-bis(butyloxycarbonylamino)toluene to 2,4-diaminotoluene in the carbamate-forming reaction described above was 86% by mol. This indicates that 99% of 2,4-bis (butyloxycarbonylamino)toluene became 2,4-tolylene diisocyanate by the thermal decomposition reaction. After completion of the carbamate-forming reaction, the thermal decomposition reaction was confirmed to be practicable only by distilling off the light-boiling fraction, without the need of eliminating or detoxifying the carbamate-forming catalyst.

While the illustrative embodiments of the present invention are provided in the above description, such is for illustrative purpose only and it is not to be construed restrictively.

Modification and variation of the present invention that will be obvious to those skilled in the art is to be covered by the following claims.

INDUSTRIAL APPLICABILITY

The present invention relates to urethane compounds and a method for producing the same, and isocyanates and a method for producing the same, and is used for industrial purposes.

The invention claimed is:

1. A method for producing urethane compounds comprising allowing a primary amine, a urea and/or an N-unsubstituted carbamate, and an alcohol to react in the presence of a compound comprising a noncoordinating anion and a metal atom as a catalyst, wherein the compound is represented by the following general formula (4):

$$MX^1{}_m X^2{}_{n-m} \quad (4)$$

wherein M represents a metal atom belonging to Groups 1 to 16 of the Periodic Table; $X^1$ represents a noncoordinating anion; $X^2$ represents a ligand; m represents an integer of 1 to n; and n represents a valence of M; such that M is zinc, and $X^1$ is an arylsulfonate anion.

2. The method for producing urethane compounds according to claim 1, wherein the primary amine is represented by the following general formula (1);

the N-unsubstituted carbamate is represented by the following general formula (2); and the alcohol is represented by the following general formula (3);

$$R^1\text{—}(NH_2)_l \quad (1)$$

(wherein $R^1$ represents an aliphatic hydrocarbon group having 1 to 15 total carbon atoms, an alicyclic-containing hydrocarbon group having 3 to 15 total carbon atoms, or an aromatic ring-containing hydrocarbon group having 6 to 15 total carbon atoms; and l represents an integer of 1 to 6)

$$R^2O\text{—}CO\text{—}N\text{—}NH_2 \quad (2)$$

(wherein $R^2$ represents an aliphatic hydrocarbon group having 1 to 16 total carbon atoms, or an aromatic hydrocarbon group having 6 to 16 total carbon atoms), and $$R^3\text{—}OH \quad (3)$$

(wherein $R^3$ represents an aliphatic hydrocarbon group having 1 to 16 total carbon atoms, or an aromatic hydrocarbon group having 6 to 16 total carbon atoms).

3. The method for producing urethane compounds according to claim 2, wherein in the general formula (1), l is 2.

4. The method for producing urethane compounds according to claim 2, wherein in the general formula (1), $R^1$ is an aromatic ring-containing hydrocarbon group having 6 to 15 total carbon atoms.

5. The method for producing urethane compounds according to claim 1, wherein an amount of the catalyst ranges from 0.000001 to 0.1 mol based on 1 mol of the primary amine.

6. A method for producing isocyanates comprising the steps of:

producing urethane compounds by the method for producing urethane compounds according to claim 1; and thermally decomposing thus-produced urethane compounds to produce isocyanates.

* * * * *